US008066243B2

(12) United States Patent
Svedman et al.

(10) Patent No.: US 8,066,243 B2
(45) Date of Patent: Nov. 29, 2011

(54) ADAPTER FOR PORTABLE NEGATIVE PRESSURE WOUND THERAPY DEVICE

(75) Inventors: Pal Svedman, Malmö (SE); David M. Tumey, Germantown, MD (US); Edward M. Litzie, Sterling, VA (US); Mark S. Meents, Germantown, MD (US); Bradley D. Yakam, Blacklick, OH (US)

(73) Assignee: Richard C. Vogel, Gaithersburg, MD (US)

( * ) Notice: Subject to any disclaimer, the term of this patent is extended or adjusted under 35 U.S.C. 154(b) by 0 days.

(21) Appl. No.: 12/684,557

(22) Filed: Jan. 8, 2010

(65) Prior Publication Data
US 2011/0168857 A1  Jul. 14, 2011

(51) Int. Cl.
*F16B 45/00* (2006.01)
(52) U.S. Cl. ........................ 248/304; 248/340
(58) Field of Classification Search .................. 248/304, 248/301, 339, 340, 311.2; 5/503.1
See application file for complete search history.

(56) References Cited

U.S. PATENT DOCUMENTS

| 2,232,254 | A | 2/1941 | Morgan |
| 2,338,339 | A | 1/1944 | LeMere et al. |
| 2,547,758 | A | 4/1951 | Keeling |
| 2,969,057 | A | 1/1961 | Simmons |
| 3,026,526 | A | 3/1962 | Montrose |
| 3,026,874 | A | 3/1962 | Stevens |
| 3,367,332 | A | 2/1968 | Groves |
| 3,478,736 | A | 11/1969 | Roberts et al. |
| 3,481,326 | A | 12/1969 | Schamblin |
| 3,486,504 | A | 12/1969 | Austin, Jr. |
| 3,610,238 | A | 10/1971 | Rich, Jr. |
| 3,682,180 | A | 8/1972 | McFarlane |
| 3,826,254 | A | 7/1974 | Mellor |
| 3,874,387 | A | 4/1975 | Barbieri |
| 3,896,810 | A | 7/1975 | Akiyama |
| 3,908,664 | A | 9/1975 | Loseff |
| 3,954,105 | A | 5/1976 | Nordby et al. |
| 3,986,649 | A * | 10/1976 | Heimstra ...................... 224/567 |
| 3,993,080 | A | 11/1976 | Loseff |
| RE29,319 | E | 7/1977 | Nordby et al. |
| 4,080,970 | A | 3/1978 | Miller |
| 4,112,947 | A | 9/1978 | Nehring |

(Continued)

FOREIGN PATENT DOCUMENTS
DE    28 09-828    9/1978
(Continued)

OTHER PUBLICATIONS

Chinn, Steven D et al., "Closed Wound Suction Drainage", The Journal of Foot Surgery, vol. 24, No. 1, 1985, pp. 76-81.

(Continued)

*Primary Examiner* — Ramon Ramirez
(74) *Attorney, Agent, or Firm* — R. William Graham

(57) ABSTRACT

A holder for a therapeutic device for treating wounds of the type having a housing equipped with a fluid mover for one of raising, compressing, or transferring fluid, and a therapeutic member operably connected to the fluid mover and actuated thereby, the therapeutic member operably disposably used on a patient in a manner to deliver therapy to the patient as a function of actuation of said fluid mover, includes a removable receiving compartment for removably receiving the device therein, and an outwardly disposed connecting surface to provide for the compartment to be suspended on an object elevated from a floor.

15 Claims, 6 Drawing Sheets

U.S. PATENT DOCUMENTS

| | | |
|---|---|---|
| 4,149,541 A | 4/1979 | Gammons et al. |
| 4,169,563 A | 10/1979 | Leu |
| 4,172,455 A | 10/1979 | Beaussant |
| 4,224,945 A | 9/1980 | Cohen |
| 4,250,882 A | 2/1981 | Adair |
| 4,256,109 A | 3/1981 | Nichols |
| 4,261,363 A | 4/1981 | Russo |
| 4,275,721 A | 6/1981 | Olson |
| 4,297,995 A | 11/1981 | Golub |
| 4,373,519 A | 2/1983 | Errede et al. |
| 4,382,441 A | 5/1983 | Svedman |
| 4,392,853 A | 7/1983 | Muto |
| 4,419,097 A | 12/1983 | Rowland |
| 4,441,357 A | 4/1984 | Kahn et al. |
| 4,469,092 A | 9/1984 | Marshall et al. |
| 4,475,909 A | 10/1984 | Eisenberg |
| 4,480,638 A | 11/1984 | Schmid |
| 4,525,166 A | 6/1985 | Leclerc |
| 4,527,064 A | 7/1985 | Anderson |
| 4,540,412 A | 9/1985 | Van Overloop |
| 4,543,100 A | 9/1985 | Brodsky |
| 4,569,674 A | 2/1986 | Phillips et al. |
| 4,573,965 A | 3/1986 | Russo |
| 4,605,399 A | 8/1986 | Weston et al. |
| 4,608,041 A | 8/1986 | Neilsen |
| 4,624,656 A | 11/1986 | Clark et al. |
| 4,640,688 A | 2/1987 | Hauser |
| 4,661,093 A | 4/1987 | Beck et al. |
| 4,710,165 A | 12/1987 | McNeil et al. |
| 4,713,052 A | 12/1987 | Beck |
| 4,743,232 A | 5/1988 | Kruger |
| 4,755,168 A | 7/1988 | Romanelli et al. |
| 4,759,354 A | 7/1988 | Quarfoot |
| 4,764,167 A | 8/1988 | Tu |
| 4,765,316 A | 8/1988 | Marshall |
| 4,778,456 A | 10/1988 | Lokken |
| 4,820,265 A | 4/1989 | DeSatnick et al. |
| 4,820,284 A | 4/1989 | Hauri |
| 4,834,110 A | 5/1989 | Richard |
| 4,836,192 A | 6/1989 | Abbate |
| 4,838,883 A | 6/1989 | Matsuura |
| 4,840,187 A | 6/1989 | Brazier |
| 4,851,545 A | 7/1989 | Song et al. |
| 4,863,449 A | 9/1989 | Therriault et al. |
| 4,878,901 A | 11/1989 | Sachse |
| 4,906,233 A | 3/1990 | Moriuchi et al. |
| 4,917,112 A | 4/1990 | Kalt |
| 4,921,492 A | 5/1990 | Schultz et al. |
| 4,925,447 A | 5/1990 | Rosenblatt |
| 4,931,519 A | 6/1990 | Song et al. |
| 4,941,882 A | 7/1990 | Ward et al. |
| 4,953,565 A | 9/1990 | Tachibana et al. |
| 4,969,880 A | 11/1990 | Zamierowski |
| 4,969,881 A | 11/1990 | Viesturs |
| 4,998,277 A * | 3/1991 | Rioux, Jr. ............ 379/454 |
| 5,035,884 A | 7/1991 | Song et al. |
| 5,086,764 A | 2/1992 | Gilman |
| 5,100,396 A | 3/1992 | Zamierowski |
| 5,106,362 A | 4/1992 | Gilman |
| 5,113,871 A | 5/1992 | Viljanto et al. |
| 5,129,615 A * | 7/1992 | Strauss ............ 248/311.2 |
| 5,149,331 A | 9/1992 | Ferdman et al. |
| 5,176,663 A | 1/1993 | Svedman |
| 5,228,431 A | 7/1993 | Giarretto |
| 5,244,175 A * | 9/1993 | Frankel ............ 248/215 |
| 5,261,893 A | 11/1993 | Zamierowski |
| 5,282,599 A * | 2/1994 | Arpaia et al. ............ 248/311.2 |
| 5,358,494 A | 10/1994 | Svedman |
| 5,527,293 A | 6/1996 | Zamierowski |
| 5,636,643 A | 6/1997 | Argenta et al. |
| 5,645,081 A | 7/1997 | Argenta et al. |
| 5,779,657 A | 7/1998 | Daneshvar |
| 6,071,267 A | 6/2000 | Zamierowski |
| 6,087,549 A | 7/2000 | Flick |
| 6,135,116 A | 10/2000 | Vogel |
| 6,142,982 A | 11/2000 | Hunt et al. |
| 6,196,992 B1 | 3/2001 | Keilman et al. |
| 6,345,623 B1 | 2/2002 | Heaton et al. |
| 6,398,767 B1 | 6/2002 | Fleischmann |
| 6,432,438 B1 | 8/2002 | Shukla |
| 6,458,109 B1 | 10/2002 | Henley et al. |
| 6,551,280 B1 | 4/2003 | Knighton et al. |
| 6,553,998 B2 | 4/2003 | Heaton et al. |
| 6,685,681 B2 | 2/2004 | Lockwood et al. |
| 6,695,823 B1 | 2/2004 | Lina et al. |
| 6,695,824 B2 | 2/2004 | Howard et al. |
| 6,752,794 B2 | 6/2004 | Lockwood et al. |
| 6,755,807 B2 | 6/2004 | Risk et al. |
| 6,800,074 B2 | 10/2004 | Henley et al. |
| 6,814,079 B2 | 11/2004 | Heaton et al. |
| 6,840,960 B2 | 1/2005 | Bubb |
| 6,841,715 B2 | 1/2005 | Roberts |
| 6,855,135 B2 | 2/2005 | Lockwood et al. |
| 6,856,821 B2 | 2/2005 | Johnson |
| 6,880,793 B2 * | 4/2005 | Huang et al. ............ 248/304 |
| 6,979,324 B2 | 12/2005 | Bybordi et al. |
| 7,004,915 B2 | 2/2006 | Boynton et al. |
| 7,022,113 B2 | 4/2006 | Lockwood et al. |
| 7,070,584 B2 | 7/2006 | Johnson et al. |
| 7,108,683 B2 | 9/2006 | Zamierowski |
| 7,117,869 B2 | 10/2006 | Heaton et al. |
| 7,144,390 B1 | 12/2006 | Hannigan et al. |
| 7,195,624 B2 | 3/2007 | Lockwood et al. |
| 7,198,046 B1 | 4/2007 | Argenta et al. |
| 7,214,202 B1 | 5/2007 | Vogel |
| 7,216,651 B2 | 5/2007 | Argenta et al. |
| 7,273,054 B2 | 9/2007 | Heaton et al. |
| 7,276,051 B1 | 10/2007 | Henley et al. |
| 7,279,612 B1 | 10/2007 | Heaton et al. |
| 7,316,672 B1 | 1/2008 | Hunt et al. |
| 7,338,482 B2 | 3/2008 | Lockwood et al. |
| 7,361,184 B2 | 4/2008 | Joshi |
| 7,381,859 B2 | 6/2008 | Hunt et al. |
| 7,422,576 B2 | 9/2008 | Boynton et al. |
| 7,438,705 B2 | 10/2008 | Karpowicz et al. |
| 7,520,872 B2 | 4/2009 | Biggie et al. |
| 7,524,286 B2 | 4/2009 | Johnson |
| 7,524,315 B2 | 4/2009 | Blott et al. |
| 7,532,953 B2 | 5/2009 | Vogel |
| 7,534,240 B1 | 5/2009 | Johnson |
| 7,534,927 B2 | 5/2009 | Lockwood et al. |
| 7,540,848 B2 | 6/2009 | Hannigan et al. |
| 7,553,306 B1 | 6/2009 | Hunt et al. |
| 2001/0031943 A1 | 10/2001 | Urie |
| 2002/0065494 A1 | 5/2002 | Lockwood et al. |
| 2003/0225355 A1 | 12/2003 | Butler |
| 2004/0002670 A1 | 1/2004 | Mothersbaugh et al. |
| 2004/0219133 A1 | 11/2004 | Lyles |
| 2005/0095723 A1 | 5/2005 | DiTrolio et al. |
| 2005/0137539 A1 | 6/2005 | Biggie et al. |
| 2005/0203469 A1 | 9/2005 | Bobroff et al. |
| 2005/0209574 A1 | 9/2005 | Boehringer et al. |
| 2005/0228329 A1 | 10/2005 | Boehringer et al. |
| 2005/0245904 A1 | 11/2005 | Estes et al. |
| 2006/0025727 A1 | 2/2006 | Boehringer et al. |
| 2006/0100586 A1 | 5/2006 | Karpowicz et al. |
| 2007/0027414 A1 | 2/2007 | Hoffman et al. |
| 2007/0032762 A1 | 2/2007 | Vogel |
| 2007/0032763 A1 | 2/2007 | Vogel |
| 2007/0219532 A1 | 9/2007 | Karpowicz et al. |
| 2010/0219312 A1* | 9/2010 | Johnson et al. ............ 248/231.81 |

FOREIGN PATENT DOCUMENTS

| | | |
|---|---|---|
| DE | 41 11 122 | 4/1993 |
| DK | 64055 | 10/1945 |
| EP | 0 880 953 | 12/1998 |
| GB | 641061 | 8/1950 |
| GB | 1273342 | 5/1972 |
| SU | 0587941 | 1/1978 |
| SU | 1268175 | 11/1986 |
| WO | 8001139 | 6/1980 |
| WO | 8905133 | 6/1989 |
| WO | WO-90/11795 | 10/1990 |
| WO | 9100718 | 1/1991 |
| WO | WO-91/16030 | 10/1991 |
| WO | WO-92/19313 | 11/1992 |

| WO | WO-92/20299 | 11/1992 |
| --- | --- | --- |
| WO | WO-96/05873 | 2/1996 |
| WO | WO/01/30422 | 5/2001 |

OTHER PUBLICATIONS

Wooding-Scott, Margaret et al., "No Wound is Too Big for Resourceful Nurses", RN, Dec. 1988, pp. 22-25.

P. Svedman, M.D., "A Dressing System Providing Fluid Supply and Suction Drainage Used for Continuous or Intermittent Irrigation", Annals of Plastic Surgery, vol. 17, No. 2, Aug. 1986, pp. 125-133.

Arnljots, Bjorn, et al. "Irrigation Treatment in Split-Thickness Skin Grafting of Intractable Leg Ulcers", Scand J Plast Reconstr Surg 19: 211-213, 1985.

Teder, H. et al., "Continuous Wound Irrigation in the Pig", Journal of Investigative Surgery, vol. 3, pp. 399-407, 1990.

Chariker M.D., Mark E., "Effective Management of Incisional and Cutaneous Fistulae with Closed Suction Wound Drainage", Contemporary Surgery, vol. 34, Jun. 1989, pp. 59-63.

Mizuno M.D., Katsuyoshi, "Suctioning Sponge", Arch Ophthalmol, vol. 101, Feb. 1983, p. 294.

Nicolov, An., "A Method of Treatment of Postphlebitic and Varicose Trophyc Ulcers of the Lower Extremities by Vacuum", 6 pages, Translation from Bulgarian into English, 1979, Surgery, XXXIV, 1981, Apr. 4, 1979.

Smith, S.R.G., et al., "Surgical Drainage", Surgical Symposium, British Journal of Hospital Medicine, Jun. 1985, pp. 308, 311, 314-315.

Westaby, S. et al., "Treatment of Purulent Wounds and Fistulae with an Adhesive Wound Irrigation Device", Instruments and Techniques, Annals of the Royal College of Surgeons of England (1981), vol. 63, pp. 353-356.

Borzov, M.V., et al., "The Vacuum Therapy of Some Skin Conditions", The Odessa N.I. Pirogov Medical Institute, Submitted, Apr. 9, 1965.

Svedman P., "Irrigation Treatment of Leg Ulcers", The Lancet, Sep. 3, 1983, pp. 532-534.

Sames, C. Patrick, "Sealing of Wounds with Vacuum Drainage". Date unknown, prior to Aug. 8, 2004.

Betancourt, M.D., Sergio, "A Method of Collecting the Effluent from Complicated Fistula of the Small Intestine". Department of Surgery, Allegheny General Hospital, Pittsburgh, p. 375. Date unknown, prior to Aug. 8, 2004.

Ramirez, Oscar M. et al., "Optimal Wound Healing Under Op-Site Dressing", Ideas and Innovations, vol. 73, No. 3, pp. 474-475, 1983.

Byers, M.D., Robert M. et al., "Clinical Effects of Closed Suction Drainage on Wound Healing in Patients with Head and Neck Cancer", Arch Otolaryngol, vol. 108, Nov. 1982, pp. 723-726.

P. Svedman et al, "Treatment of leg ulcers by intermittent irrigation through a felt dressing", IRCS Med. Sci., 13, 489-490 (1985).

P. Svedman, "A Dressing Allowing Continuous Treatment of a Biosurface", IRCS Medical Science: Biomedical Technology; Clinical Medicine; Surgery and Transplantation, 7, 221 (1979).

Egnell Minor, Instruction book, First Edition, 300 7502 [Feb. 1975] (w/ partial English Translation).

Addition to the Users Manual Concerning Overflow Protection concerns all Egnell pumps, dated Feb. 3, 1983 (w/partial English translation).

Wolthuis et al., "Physiological Effects of Locally applied Reduced Pressure in Man," Physiological Reviews, 54: 566-595, Jul. 1974.

Lundvall et al., "Transmission of externally applied negative pressure of the underlying tissue. A study on the upper arm of man," Acta Physiol Scand, 136: 403-409, accepted Jan. 28, 1989.

Dunlop et al., "Vacuum drainage of groin wounds after vascular surgery: a controlled trial," Br. J. Surg., 77: 562-563 (1990).

Bucalo et al., "Inhibition of cell proliferation by chronic wound fluid," Wound Repair and Regeneration, Miami, 1993, 181-186.

Urschel et al., "The effect of mechanical stress on soft and hard tissue repair; a review," British Journal of Plastic Surgery, 41, 182-186, 1988.

Jeter, K.R. et al. (eds.), "Managing Draining Wounds And Fistulae: New And Established Methods," Chronic Wound Care: Health Management Publications, 1990, pp. 240-246.

Fleischmann, W., Wund Forum Spezial. IHW '94. "Vakuumversiegelung zur Behandlung von Problemwunden," (English translation: Vacuum sealing for Treatment of Problematical Wounds.).

Fleischmann, W. et al., Acta Orthopaedica Belgica. vol. 58, Suppl. I-1992, "Treatment of Bone and Soft Tissue Defects in Infected Nonunion."

Fleischmann, W. et al., Unfall Chirurgie, Springer-Varlag 1993, "Vakuumversiegelung zur Behandlung des Weichteilschadens bei offenen Frakturen."

Valenta, A., American Journal of Nursing, Apr. 1994, "Using the Vacuum Dressing Alternative for Difficult Wounds."

Mulder, G.D. et al. (eds.), Clinicians' Pocket Guide to Chronic Wound Repair, (Spartanburg, SC: Wound Healing Publications), 1991, pp. 54-55.

Morykwas, M. et al., "Use of Negative Pressure to Increase the Rate of Granulation Tissue Formation in Chronic Open Wounds," Extracellular Matrix and Healing, pp. 800, 1993.

Schneider, A. et al., "A New and Reliable Method of Securing Skin Grafts to the Difficult Recipient Bed," Plastic and Reconstructive Surgery, vol. 102(4), Sep. 1998, pp. 1195-1198.

Morykwas, M. et al., "Nonsurgical Modalities to Enhance Healing and Care of Soft Tissue Wounds," Journal of the Southern Orthopaedic Association, vol. 6, No. 4, Winter 1997, pp. 279-288.

Tittle, K. et al., "VariDyne—new standards in postoperative wound drainage," Unfall Chirurgie, 1988, 14(2):104-107.

Genecov, A. et al., "A Controlled Subatmospheric Pressure Dressing Increases the Rate of Skin Graft Donor Site Reepithelialization," Annals of Plastic Surgery, col. 40, No. 3, Mar. 1998, pp. 219-225.

Morykwas, M. et al., "Vacuum Assisted Closure: A New Method for Wound Control and Treatment: Animal Studies and Basic Foundation"—Annals of Plastic Surgery, vol. 38, No. 6, Jun. 1997.

Argenta, L. et al., "Vacuum-Assisted Closure: A New Method for Wound Control and Treatment: Clinical Experience," Annals of Plastic Surgery, vol. 38, No. 6, Jun. 1997.

Neumann, P. et al., "Gelatin-based sprayable foam as a skin substitute." Journal of Biomedical Materials Research, 1981; vol. 15, pp. 9-18.

N. A. Bagautdinov, "Variant of External Vacuum Aspiration in the Treatment of Purulent Diseases of Soft Tissue", Current Problems in Modern Clinical Surgery, 1986; pp. 94-96.

N. A. Bagautdinov, et al., "Vacuum and Vacuum Sorption Treatment of Open Septic Wounds", USSR Ministry of Health USSR Academy of Medical Sciences A.V. Vyshnevsky Institute of Surgery of the USSR AMS, 1986, pp. 91-92.

\* cited by examiner

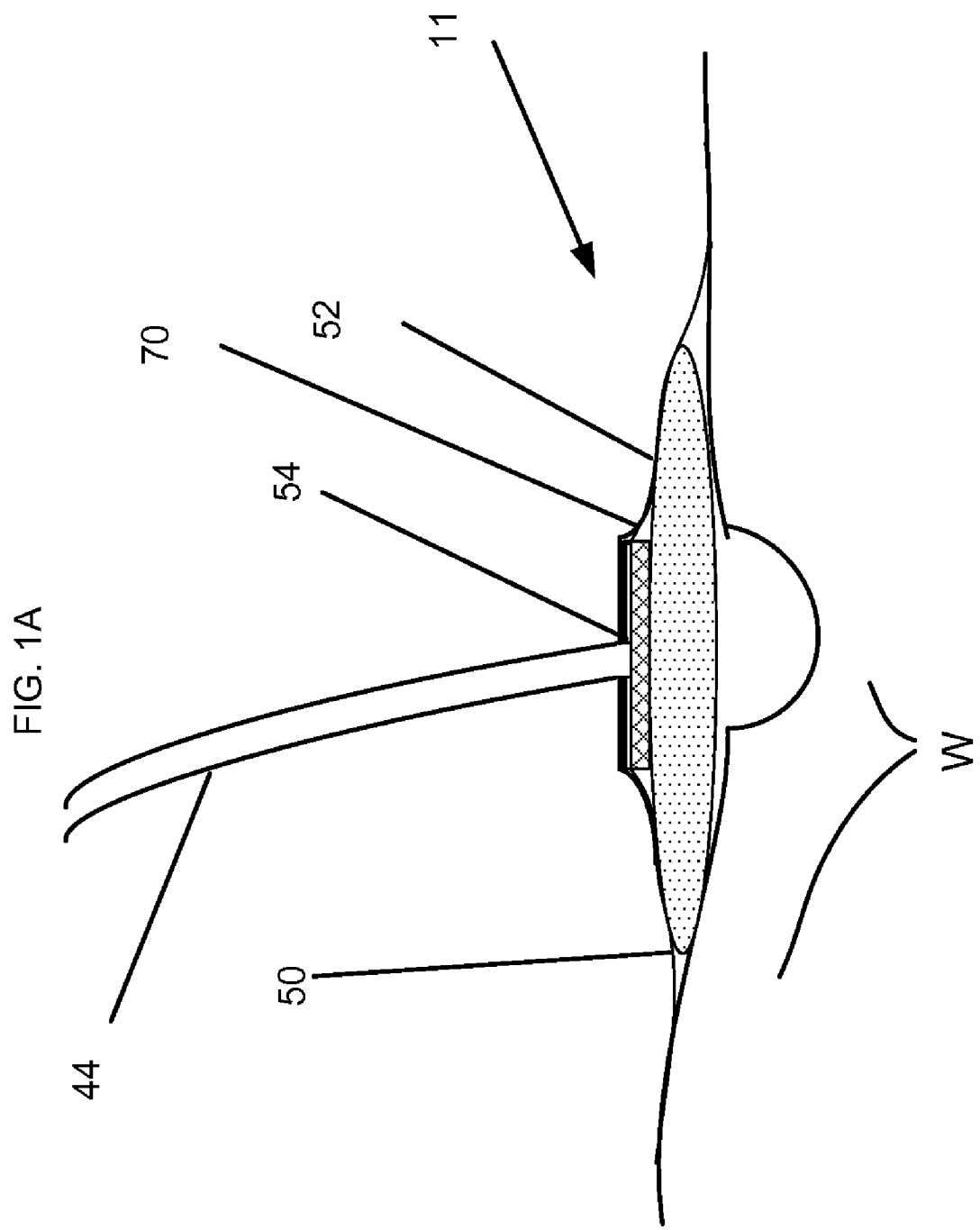

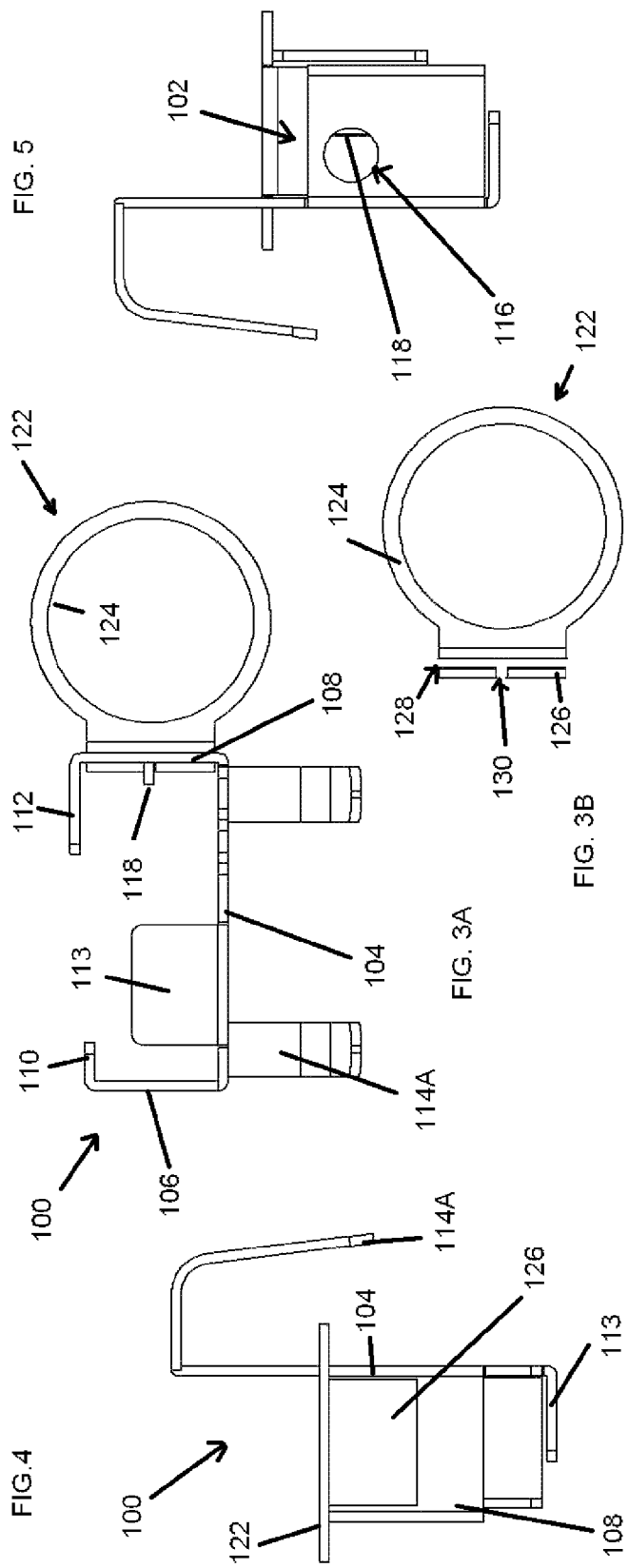

ADAPTER FOR PORTABLE NEGATIVE PRESSURE WOUND THERAPY DEVICE

BACKGROUND OF INVENTION

1. Field of Invention

The invention is generally directed to a therapeutic device for the promotion of wound healing. More particularly, the present invention relates to an adapter such as a holder for a therapeutic device of the type providing fluid irrigation and vacuum drainage of a wound.

2. Related Art

These devices are normally used in clinical settings such as hospitals or extended care facilities, but patients can often be located in non-clinical environments, where portability, ease of use, and control of therapy parameters is necessary. Such places can, for example, include the home, office or motor vehicles, and at the extreme, military battlefields and other locations where electrical power may be unreliable or unavailable.

Negative pressure wound therapy (NPWT), also known as vacuum drainage or closed-suction drainage, is known. A vacuum source is connected to a semi-occluded or occluded therapeutic member, such as a compressible wound dressing. Various porous dressings comprising gauze, felts, foams, beads and/or fibers can be used in conjunction with an occlusive semi-permeable cover and a controlled vacuum source. In addition to negative pressure, there exist pump devices configured to supply positive pressure to another therapeutic member, such as an inflatable cuff for various medical therapies.

In addition to using negative pressure wound therapy, many devices employ concomitant wound irrigation. For example, a known wound healing apparatus includes a porous dressing made of polyurethane foam placed adjacent a wound and covered by a semi-permeable and flexible plastic sheet. The dressing further includes fluid supply and fluid drainage connections in communication with the cavity formed by the cover, foam and skin. The fluid supply is connected to a fluid source that can include an aqueous topical anesthetic or antibiotic solution, isotonic saline, or other medicaments for use in providing therapy to the wound. The fluid drainage can be connected to a vacuum source where fluid can be removed from the cavity and subatmospheric pressures can be maintained inside the cavity. The wound irrigation apparatus, although able to provide efficacious therapy, is somewhat cumbersome, difficult to use without trained professional medical personnel, and generally impractical outside the clinical setting. Such a device does not address various factors concerning patients outside clinical settings.

Some devices use vacuum sealing of wound dressings consisting of polyvinyl alcohol foam cut to size and stapled to the margins of the wound. Such dressings are covered by a semi-permeable membrane while suction and fluid connections are provided by small plastic tubes which are introduced into the foam generally through the patient's skin. Such devices alternate in time between vacuum drainage and the introduction of aqueous medicaments to the wound site, but do not do both simultaneously. While the prior devices have proven to be useful in fixed therapeutic sites, such devices require improvement to render broader and friendlier use.

SUMMARY OF THE INVENTION

It is an object to improve wound healing.
It is another object to improve devices for use in treating wounds.
It is an object to improve a pump for use in treating wounds.
It is yet another object to provide a therapeutic device for treating wounds which has improved portability.
It is yet another object to provide a therapeutic device for treating wounds which has improved ease of use.
It is yet another object to provide an adapter or holder for a therapeutic device for treating wounds.

One embodiment of the invention is directed to an adapter or holder for a therapeutic device for treating wounds of the type having a housing equipped with a fluid mover for one of raising, compressing, or transferring fluid, and a therapeutic member operably connected to the fluid mover and actuated thereby, the therapeutic member operably disposably used on a patient in a manner to deliver therapy to the patient as a function of actuation of said fluid mover, which includes a removable receiving compartment configured with at least one side surface for removably receiving the therapeutic device therein, and an object connecting surface extending from the side to provide for the compartment to be suspended on an object elevated from a floor. The object can be a bed foot board or side rail wherein the object connecting surface includes one or more angled arms. Optionally, the object can be an erect mobile pole, such as an IV pole, wherein the object connecting surface includes one or more open surfaces formed in an outer side of the compartment.

In one embodiment, the holder compartment is configured to removably retain the therapeutic device and an associated collection canister. In another embodiment, there is provided a canister receptacle which is preferably removably connected to the compartment to extend outside the device compartment to removably retain a canister external thereto and in this regard can be a secondary canister which is used in conjunction with the device.

The device compartment can include a retaining member which includes a pair of opposing sides which are equipped with surfaces configured to removably secure the device within the compartment. In a preferred embodiment, one of the sides is configured with an open surface of a size to receive a protruding portion of the therapeutic device while the other side is configured with an inwardly extending surface having a tapered upper end which permits ease of insertion of the device into the compartment such that as the device is inserted into the compartment the protruding portion of the device is forced into the open receiving surface and upon being fully seated the device is substantially retained within the compartment and requires canting of the device to gain release from the compartment.

BRIEF DESCRIPTION OF THE DRAWINGS

FIG. 1A depicts a part of the invention.
FIG. 3A is a bottom view of FIG. 2.
FIG. 3B depicts a bottom view of another part of FIG. 2
FIG. 4 is a right side view of FIG. 2.
FIG. 5 is a left side view of FIG. 2.

DETAILED DESCRIPTION

Figure 1:
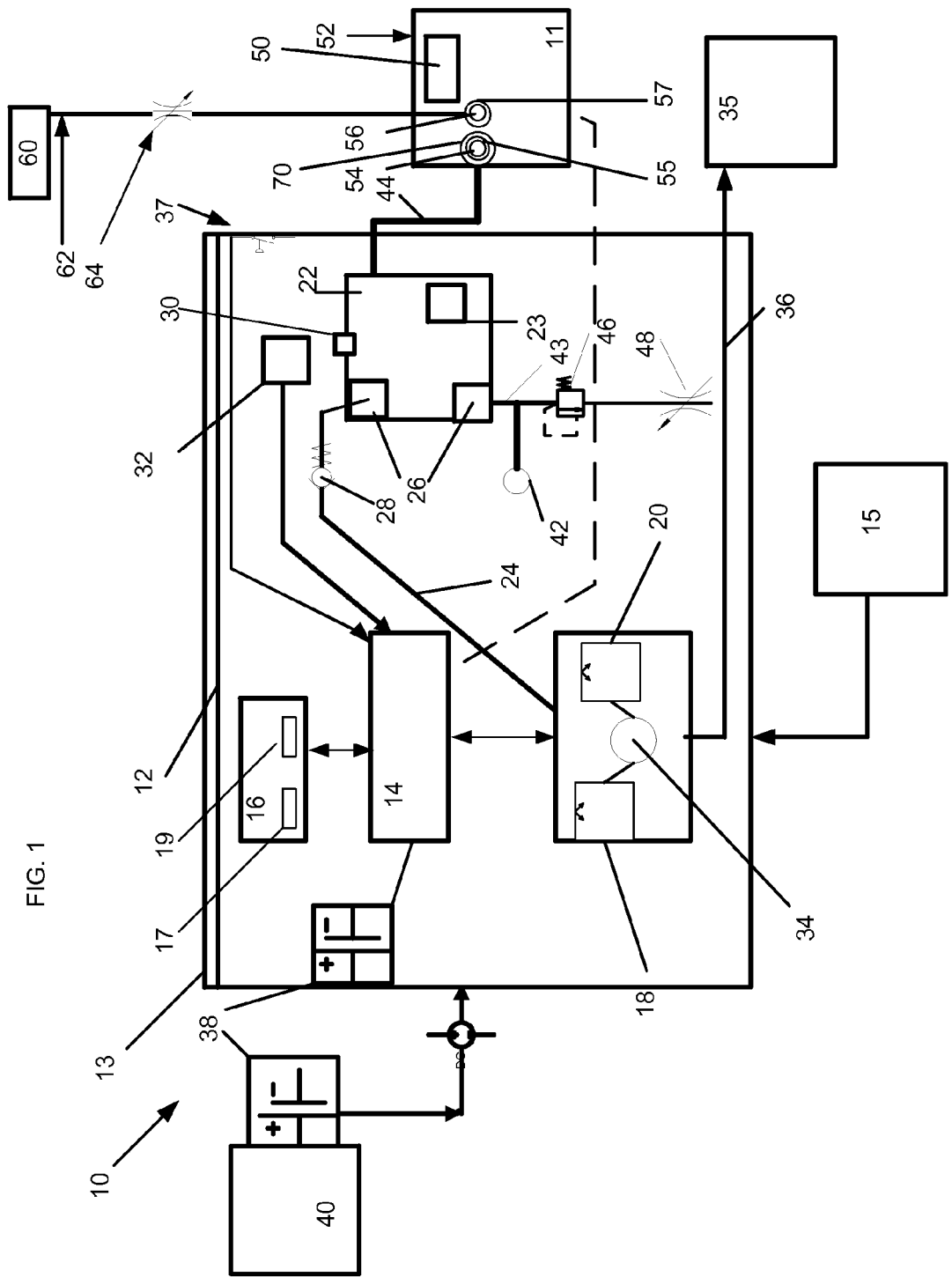
FIG. 1 is a schematic illustrating the device of the invention.

As illustrated in FIG. 1, a disposable therapeutic device of the instant invention is generally designated by the numeral 10. The disposable therapeutic device 10 can preferably include a housing 12 which provides an improved therapeutic device with multiple uses and portability. The housing 12 can preferably be formed in a waterproof manner to protect components therein. In this regard, housing 12 can have a watertight sealed access panel 13 through which components can be accessed.

The device 10 can include a processor 14, which can be a microcontroller having an embedded microprocessor, Random Access Memory (RAM) and Flash Memory (FM). FM can preferably contain the programming instructions for a control algorithm. FM can preferably be non-volatile and retains its programming when the power is terminated. RAM can be utilized by the control algorithm for storing variables such as pressure measurements, alarm counts and the like, which the control algorithm uses while generating and maintaining the vacuum.

A membrane keypad and a light emitting diode LED or liquid crystal display (LCD) 16 can be electrically associated with processor 14 through a communication link, such as a cable. Keypad switches provide power control and are used to preset the desired pressure/vacuum levels. Light emitting diodes 17, 19 can be provided to indicate alarm conditions associated with canister fluid level, leaks of pressure in the dressing and canister, and power remaining in the power source.

Microcontroller 14 is electrically associated with, and controls the operation of, a first vacuum pump 18 and an optional second vacuum pump 20 through electrical connections. First vacuum pump 18 and optional second vacuum pump 20 can be one of many types including, for example, the pumps sold under the trademarks Hargraves® and Thomas®. Vacuum pumps 18 and 20 can use, for example, a reciprocating diaphragm or piston to create vacuum and can be typically powered by a direct current (DC) motor that can also optionally use a brushless commutator for increased reliability and longevity. Vacuum pumps 18 and 20 can be pneumatically associated with a disposable exudate collection canister 22 through a single-lumen tube 24.

In one embodiment, canister 22 has a volume which does not exceed 1000 ml. This can prevent accidental exsanguination of a patient in the event hemostasis has not yet been achieved at the wound site. Canister 22 can be of a custom design or one available off-the-shelf and sold under the trademark DeRoyal®.

An adapter or holder 100 for the therapeutic device 10 includes a removable receiving compartment 102. The compartment 102 can be configured with at least one side surface, here shown with back side surface 104, side surfaces 106 and 108, front side surfaces 110 and 112, and bottom side surfaces 113 for removably receiving the therapeutic device 10 therein and can be sized to accommodate the housing 12 and canister 22 accordingly.

Figure 2:
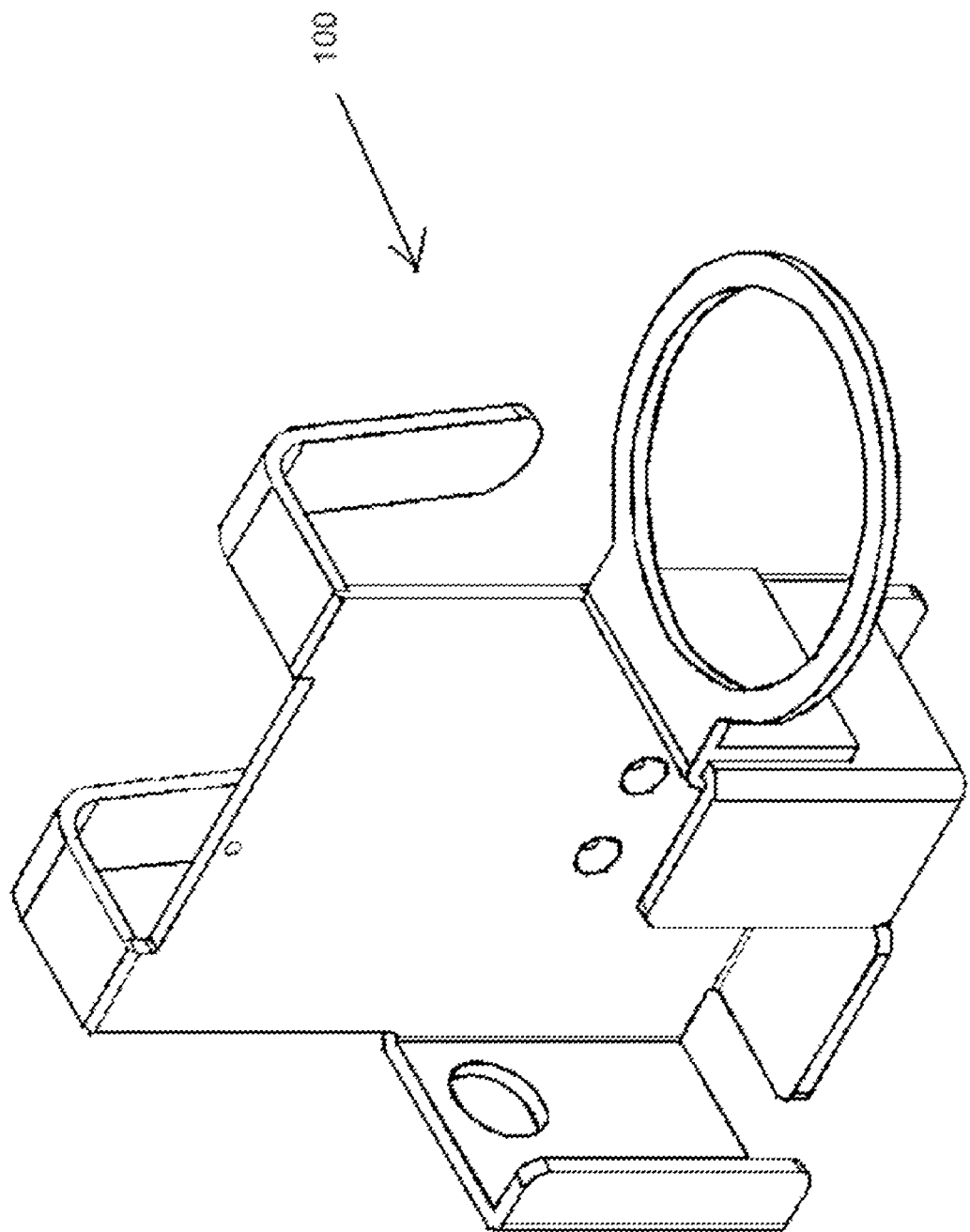
FIG. 2 depicts a perspective view of a holder of the invention.
Figure 8:
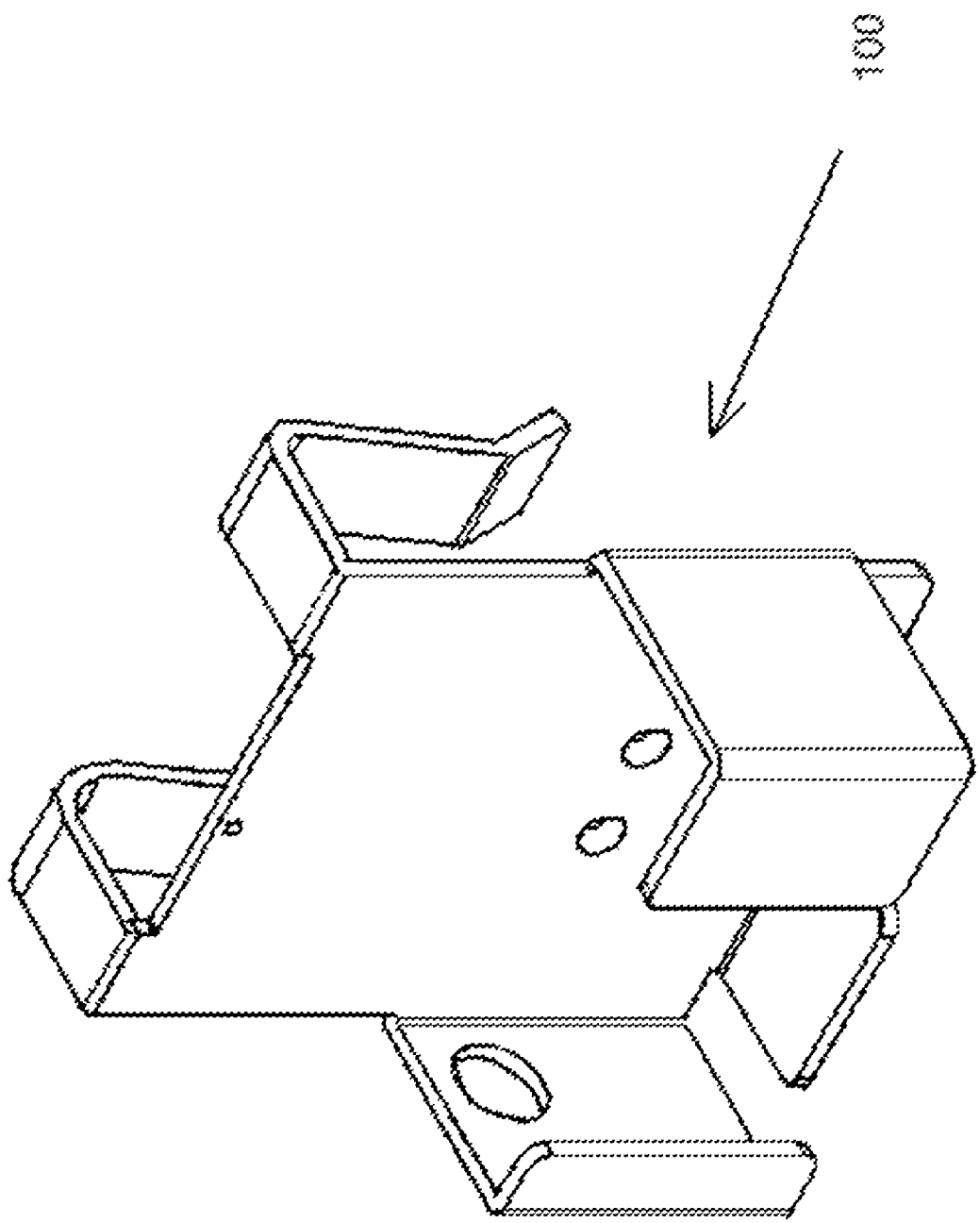
FIG. 8 depicts another perspective view of a holder of the invention.

There can be provided one or more object connecting surfaces 114 extending from the back side surface 104 to provide for the compartment 102 to be suspended on an object elevated from a floor. For example, the object connecting surfaces 114 can include arms 114A as seen in FIG. 2 or arms 114B as seen in FIG. 8 which differ from arms 114A in a different flared end. The object to which the arms 114A or 114B connect can be a hospital bed foot board or side rail. Optionally, the object can be an erect mobile pole, such as an IV pole, wherein the object connecting surface 114 includes one or more open surfaces 114C formed in back side surface 102 of the compartment 102 to which various pole clamping mechanisms, well known to anyone of ordinary skill in the art, can be attached.

The device compartment 102 can be characterized to include a retaining member which includes a pair of opposing sides, such as side surfaces 106 and 108 which are equipped with surfaces configured to removably secure the device 10 within the compartment 102. In a preferred embodiment, the side surface 106 can be configured with an open surface 116 of a size to receive a protruding portion 117 of the therapeutic device 10 while the side surface 108 is configured with an inwardly extending member 118 having a tapered upper end 120 which permits ease of insertion of the device 10 into the compartment 102 such that as the device 10 is inserted into the compartment 102 the protruding portion 117 of the device 10 is directed into the open receiving surface 116 and upon being fully seated the device 10 is substantially retained within the compartment 102 and requires canting of the device 10 to gain release from the compartment 102.

Figure 6:
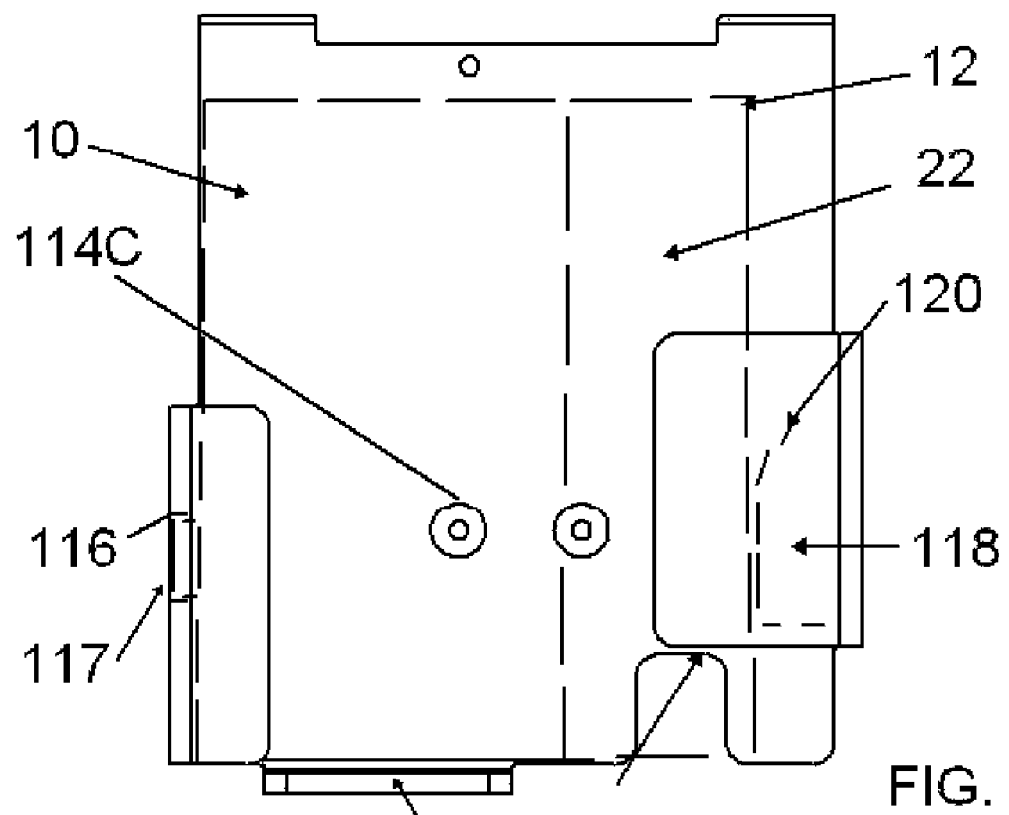
FIG. 6 is a front view of a part of FIG. 2.
Figure 7:
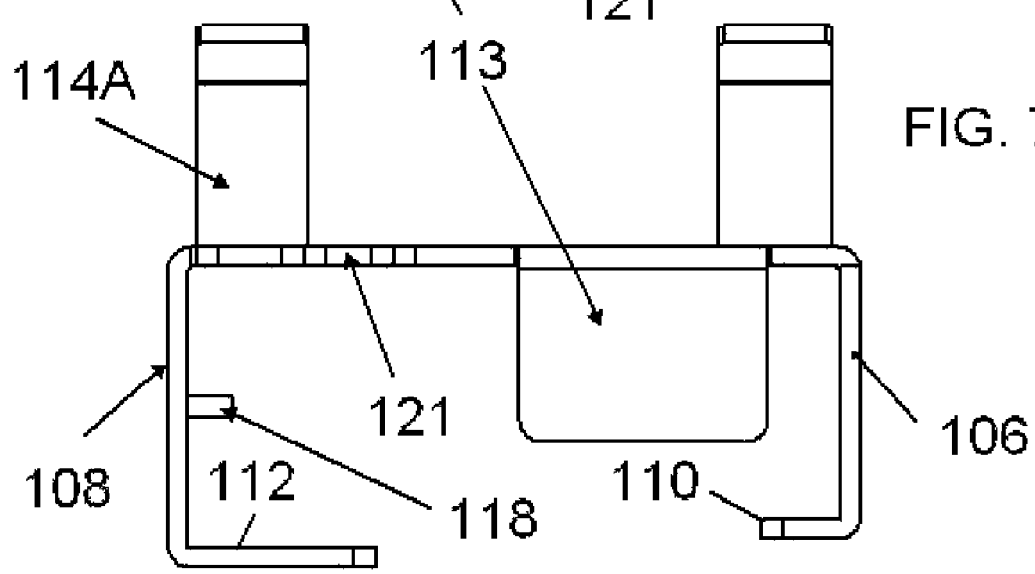
FIG. 7 is a top view of FIG. 6.

In one embodiment as represented in FIG. 6, for example, the holder compartment 102 is configured to removably retain the therapeutic device 10 and an associated collection canister 22 which is a primary collection container of the device 10. In this case, there is also provided a notched surface 121 in the back side surface 104 which creates an opening to canister 22 for a thumb and finger to grip and pull the canister 22 out of the device 10 while the device 10 is inside the holder 100. The notched surface 121 is there to permit access to the bottom of the canister 22 and is intended to co-align with similar a notched surface in a canister shield of device housing 12.

In another embodiment, there is provided a canister receptacle 122 which can be removably connected to side surface 108 of the compartment 102 to extend outside thereof to removably retain a canister, which may be a secondary canister, external to holder 100 and which can be used in conjunction with the device 10. The canister receptacle 122 can include a retaining enclosure ring 124 which is connected to a clip end 126 which includes a lengthwise slot 128 to receive the side surface 108 and a medial slot 130 to receive the inwardly extending member 118.

Referring now again to FIG. 1, a fluid barrier 26, which can be a back flow valve or filter, is associated with canister 22 and is configured to prevent fluids collected in canister 22 from escaping into tubing 24 and fouling the vacuum return path. Barrier 26 can be of a mechanical float design or may have one or more membranes of hydrophobic material such as those available under the trademark GoreTex™. Barrier 26 can also be fabricated from a porous polymer such as that which is available under the trademark MicroPore™. A secondary barrier 28 using a hydrophobic membrane or valve is inserted in-line with pneumatic tubing 24 to prevent fluid ingress into the system in the event barrier 26 fails to operate as intended. Pneumatic tubing 24 can connect to first vacuum pump 18 and optional second vacuum pump 20 through "T" connectors.

An identification member 30, such as radio frequency identification (RFID) tag, can be physically associated with the canister 22 and an RFID sensor 32 operably associated with the microcontroller 14 such that the microcontroller 14 can restrict use of the device 10 to a predetermined canister 22. Thus, if a canister 22 does not have a predetermined RFID chip, the device 10 will not operate. Another embodiment envisions software resident on microcontroller 14 which restricts the use of the device 10 to a predetermined time period such as 90 days for example. In this way, the patient using the device 10 may use the device 10 for a prescribed time period and then the device 10 automatically times out per a particular therapeutic plan for that patient. This also enables a reminder of the time and date for the next dressing change or physician appointment. It is also contemplated that the microcontroller 14 be operably provided with a remote control 15 and communication link, such as a transceiver, wherein the device 10 can be shut down remotely when a particular therapeutic plan for that patient has ended. Likewise, remote control 15 can be utilized to provide additional time after the therapeutic device times out.

Vacuum-pressure sensor 34 is pneumatically associated with first vacuum pump 18 and optional vacuum pump 20 and electrically associated with microcontroller 14. Pressure sensor 34 provides a vacuum-pressure signal to the microprocessor enabling a control algorithm to monitor vacuum pressure at the outlet of the vacuum pumps 18 and 20.

An acoustic muffler can be provided and pneumatically associated with the exhaust ports of vacuum pumps 18 and 20 and configured to reduce exhaust noise produced by the pumps during operation. In normal operation of device 10, first vacuum pump 18 can be used to generate the initial or "draw-down" vacuum while optional second vacuum pump 20 can be used to maintain a desired vacuum within the system compensating for any leaks or pressure fluctuations. Vacuum pump 20 can be smaller and quieter than vacuum pump 18 providing a means to maintain desired pressure without disturbing the patient. It is contemplated by the instant invention that pumps 18 and 20 can also be employed to create a positive pressure for purposes of applying pressure to an inflatable member 35, such as a cuff or pressure bandage, through tubing 36. A switch 37 can be operatively disposed on housing 12 in operable connection with microcontroller 14 to enable selection of positive and negative pressure from pumps 18/20.

One or more battery (ies) 38 can preferably be provided to permit portable operation of the device 10. Battery 38 can be Lithium Ion (LiIon), Nickel-Metal-Hydride (NiMH), Nickel-Cadmium, (NiCd) or their equivalent, and can be electrically associated with microcontroller 14 through electrical connections. Battery 38 can be of a rechargeable type which is preferably removably disposed in connection with the housing 12 and can be replaced with a secondary battery 38 when needed. A recharger 40 is provided to keep one battery 38 charged at all times. Additionally, it is contemplated that the device 10 can be equipped to be powered or charged by recharger 40 or by circuits related with microcontroller 14 if such source of power is available. When an external source of power is not available and the device 10 is to operate in a portable mode, battery 38 supplies power to the device 10. The battery 38 can be rechargeable or reprocessable and can preferably be removably stored in a waterproof manner within housing 12 which also likewise contains the pumps 18, 20 and microcontroller 14.

A second pressure sensor 42 is pneumatically associated with canister 22 through a sensor port 43. Pressure sensor 42 can be electrically associated with microcontroller 14 and provides a vacuum-pressure signal to microprocessor enabling control algorithm to monitor vacuum pressure inside canister 22 and dressing 11. A "T" connector can be connected to port 43, to pressure sensor 42 and a vacuum-pressure relief solenoid 46 configured to relieve pressure in the canister 22 and dressing 11 in the event of an alarm condition, or if power is turned off. Solenoid 46, can be, for example, one available under the trademark Parker Hannifin® or Pneutronics®; Solenoid 46 is electrically associated with, and controlled by, microprocessor of microcontroller 14. Solenoid 46 can be configured to vent vacuum pressure to atmosphere when an electrical coil associated therewith is de-energized as would be the case if the power is turned off. An orifice restrictor 48 may optionally be provided in-line with solenoid 46 and pneumatic tube 44 to regulate the rate at which vacuum is relieved to atmospheric pressure when solenoid 46 is de-energized. Orifice restrictor 48 is, for example, available under the trademark AirLogic®.

A wound dressing 11 can preferably include a sterile porous substrate 50, which can be a polyurethane foam, polyvinyl alcohol foam, gauze, felt or other suitable material, a semi-permeable adhesive cover 52 such as that sold under the trademark DeRoyal® or Avery Denison®, an inlet port 56 and a suction port 54. Substrate 50 is configured to distribute vacuum pressure evenly throughout the entire wound bed and has mechanical properties suitable for promoting the formation of granular tissue and approximating the wound margins.

In addition, when vacuum is applied to dressing 11, substrate 50 creates micro- and macro-strain at the cellular level of the wound stimulating the production of various growth factors and other cytokines, and promoting cell proliferation. Dressing 11 is fluidically associated with canister 22 through single-lumen tube 44. The vacuum pressure in a cavity formed by substrate 50 of dressing 11 is largely the same as the vacuum pressure inside canister 22 minus the weight of any standing fluid inside tubing 44.

A fluid vessel 60, which can be a standard IV bag, contains medicinal fluids such as aqueous topical antibiotics, analgesics, physiologic bleaches, or isotonic saline. Fluid vessel 60 is removably connected to dressing 11 though port 56 and single-lumen tube 62.

An optional flow control device 64 can be placed in-line with tubing 62 to permit accurate regulation of the fluid flow from vessel 60 to dressing 11. In normal operation, continuous wound site irrigation is provided as treatment fluids move from vessel 60 through dressing 11 and into collection canister 22. This continuous irrigation keeps the wound clean and helps to manage infection. In addition, effluent produced at the wound site and collected by substrate 50 will be removed to canister 22 when the system is under vacuum.

The device 10 is particularly well suited for providing therapeutic wound irrigation and vacuum drainage and provides for a self-contained plastic housing configured to be worn around the waist or carried in a pouch over the shoulder for patients who are ambulatory, and hung from the footboard or headboard of a bed for patients who are non-ambulatory. Membrane keypad and display 16 is provided to enable the adjustment of therapeutic parameters and to turn the unit on and off.

Depressing the power button on membrane switch 16 will turn the power to device 10 on/off. While it is contemplated that the membrane switch 16 be equipped with keys to adjust therapeutic pressure up and down, the microcontroller 14 can preferably be equipped to control the pressure in accordance with sensed pressure and condition to maintain pressure in an operable range between −70 mmHg and −150 mmHg with a working range of between 0 and −500 mmHg, for example. Although these pressure settings are provided by way of example, they are not intended to be limiting because other pressures can be utilized for wound-type specific applications. The membrane 16 can also be equipped with LED 17 to indicate a leak alarm and/or LED 19 indicates a full-canister alarm. When either alarm condition is detected, these LEDs will light in conjunction with an audible chime which is also included in the device 10.

Housing 12 can incorporate a compartment configured in such a way as to receive and store a standard IV bag 60 or can be externally coupled to thereto. IV bag 60 may contain an aqueous topical wound treatment fluid that is utilized by the device 60 to provide continuous irrigation. A belt clip can provided for attaching to a patient's belt and an optional waist strap or shoulder strap is provided for patients who do not or cannot wear belts.

Canister 22 is provided for exudate collection and can preferably be configured as currently known in the field with a vacuum-sealing means and associated fluid barrier 26, vacuum sensor port 43 and associated protective hydrophobic filter, contact-clear translucent body, clear graduated measurement window, locking means and tubing connection means. Collection canister 22 typically has a volume less than 1000 ml to prevent accidental exsanguination of a patient if hemostasis is not achieved in the wound. Fluid barriers 26 can be, for example, those sold under the trademark MicroPore® or GoreTex® and ensure the contents of canister 22 do not inadvertently ingress into pumps 18, 20 of housing 12 and subsequently cause contamination of thereof.

Pressure sensor 42 enables microcontroller 14 to measure the pressure within the canister 22 as a proxy for the therapeutic vacuum pressure under the dressing 11.

Optionally, tubing 62 can be multilumen tubing providing one conduit for the irrigation fluid to travel to dressing 11 and another conduit for the vacuum drainage. Thus, IV bag 60, tubing 62, dressing 11 and canister 22 provide a closed fluid pathway. In this embodiment, canister 22 would be single-use disposable and may be filled with a solidifying agent 23 to enable the contents to solidify prior to disposal. Solidifying agents are available, for example, under the trademark DeRoyal® and Isolyzer®. The solidifying agents prevent fluid from sloshing around inside the canister particularly when the patient is mobile, such as would be the case if the patient were travelling in a motor vehicle. In addition, solidifying agents are available with antimicrobials that can destroy pathogens and help prevent aerosolization of bacteria.

At the termination of optional multilumen tubing 62, there can be provided a self-adhesive dressing connector 57 for attaching the tubing to drape 52 with substantially air-tight seal. Dressing connector 11 can have an annular pressure-sensitive adhesive ring with a release liner that is removed prior to application. Port 56 can be formed as a hole cut in drape 52 and dressing connector 57 would be positioned in alignment with said hole. This enables irrigation fluid to both enter and leave the dressing through a single port. In an alternative embodiment, tube 62 can bifurcate at the terminus and connect to two dressing connectors 57 which allow the irrigation port to be physically separated from the vacuum drainage port thus forcing irrigation fluid to flow though the entire length of the dressing if it is so desired. Similarly, port 54 and connector 55 can be provided to connect optional multilumen tubing 44 to dressing 11. In this arrangement, the second lumen may be used to directly measure the pressure in dressing 11.

Fluid vessel 60 can be of the type which includes a self-sealing needle port situated on the superior aspect of the vessel 60 and a regulated drip port situated on the inferior aspect of the vessel. The needle port permits the introduction of a hypodermic needle for the administration of aqueous topical wound treatment fluids. These aqueous topical fluids can include a topical anesthetic such as Lidocaine, antibiotics such as Bacitracin or Sulfamide-Acetate; physiologic bleach such as Chlorpactin or Dakins solution; and antiseptics such as Lavasept or Octenisept. Regulated drip port permits fluid within vessel 60 to egress slowly and continuously into porous substrate 50 whereupon the therapeutic benefits can be imparted to the wound site. Single-lumen drainage tube 44 provides enough vacuum to keep the dressing 11 at sub-atmospheric pressure and to remove fluids, which include the irrigation fluid and wound exudates. With this modification, the need for an external fluid vessel and associated tubing and connectors can be eliminated making the dressing more user friendly for patient and clinician alike.

In typical clinical use of this alternate embodiment, dressing 11 is applied to the wound site by first cutting porous substrate 50 to fit the margins of the wound. Next, semi-permeable drape 52 is attached and sealed over the dressing and periwound. A hole approximately ⅜" diameter can be made in drape 52 central to porous substrate 50. Fluid vessel 60 is attached by adhesive annular ring 57 with port 56 aligned with the hole previously cut in drape 52. Once the fluid vessel 60 is hermetically sealed to the drape 52, a properly prepared hypodermic needle is inserted in self-sealing needle port and fluid vessel 60 subsequently filled with the desired aqueous topical wound treatment solution.

For the majority of applications, the technique for providing therapeutic wound irrigation and vacuum drainage is illustrated. The single lumen drainage tube 44 is provided for the application of vacuum and removal of fluids from the wound site. Fluid vessel 60 can be situated outside and superior to semi-permeable substrate 50. An annular adhesive ring 57 is provided on port 56 for attachment of single-lumen irrigation tubing 62 to drape 52. Similarly, a needle port permits the introduction of a hypodermic needle for the administration of aqueous topical wound treatment fluids as described above, for example, a caregiver may want to add a topical antibiotic to a bag of isotonic saline. Adjustable optional flow control device 64 permits fluid within vessel 60 to egress slowly and continuously into porous substrate 50 through hole 56 in drape 52 whereupon the therapeutic benefits can be imparted to the wound site. Single-lumen drainage tube 44 provides enough vacuum to keep the dressing 11 at sub-atmospheric pressure and to remove fluids which include the irrigation fluid and wound exudates.

Because of the potential chemical interactions between the various materials used in the construction of dressing 11, attention must be paid to the types of aqueous topical wound fluids used to ensure compatibility.

The above described embodiments are set forth by way of example and are not limiting. It will be readily apparent that obvious modifications, derivations and variations can be made to the embodiments. For example, the vacuum pumps described having either a diaphragm or piston-type could also be one of a syringe based system, bellows, or even an oscillating linear pump. Accordingly, the claims appended hereto should be read in their full scope including any such modifications, derivations and variations.

What is claimed is:

1. A holder for a therapeutic device for treating wounds of the type having a housing equipped with a fluid mover for one of raising, compressing, or transferring fluid, a therapeutic member operably connected to the fluid mover and actuated thereby, the therapeutic member operably disposably used on a patient in a manner to deliver therapy to the patient as function of actuation of said fluid mover, which includes:

a removable receiving compartment configured with side surfaces, a bottom surface and a back surface for removably receiving the therapeutic device therein, and an object connecting surface extending from said back surface to provide for said compartment to be suspended on an object elevated from a floor whereupon so doing the therapeutic device is suspended when received in said compartment, and a canister container which is removably connected to said compartment in a manner to extend outside the device compartment to removably retain a canister external thereto.

2. The holder for a therapeutic device of claim 1, wherein said object connecting surface includes one or more angled arms to enable hanging on a bed foot board.

3. The holder for a therapeutic device of claim 1, wherein said device compartment is configured to removably retain the housing of therapeutic device and an associated collection canister.

4. The holder for a therapeutic device of claim 3, wherein said side surface includes a notched surface to aid in removal of the collection canister from the therapeutic device.

5. The holder for a therapeutic device of claim 1, wherein said compartment includes a retaining member.

6. A holder for a therapeutic device for treating wounds of the type having a housing equipped with a fluid mover for one of raising, compressing, or transferring fluid, and a therapeutic member operably connected to the fluid mover and actuated thereby, the therapeutic member operably disposably used on a patient in a manner to deliver therapy to the patient as function of actuation of said fluid mover, which includes:
   a removable receiving compartment configured with side surfaces, a bottom surface and a back surface for removably receiving the therapeutic device therein for removably receiving the therapeutic device therein, and an object connecting surface extending through said side to provide for said compartment to be suspended on an object elevated from a floor whereupon so doing the therapeutic device is suspended when received in said compartment and
   a canister container which is removably connected to said compartment in a manner to extend outside the device compartment to removably retain a canister external thereto.

7. The holder for a therapeutic device of claim 6, wherein said object connecting surface includes at least one open surface formed in said side surface of said compartment to enable connection to an erect mobile pole.

8. The holder for a therapeutic device of claim 6, wherein said device compartment is configured to removably retain the housing of therapeutic device and an associated collection canister.

9. The holder for a therapeutic device of claim 8, wherein said side surface includes a notched surface to aid in removal of the collection canister from the therapeutic device.

10. The holder for a therapeutic device of claim 6, wherein said compartment includes a retaining member.

11. The holder for a therapeutic device of claim 10, wherein said retaining member includes a pair of opposing sides which are equipped with surfaces configured to removably secure the device within the compartment.

12. The holder for a therapeutic device of claim 11, wherein one of the sides is configured with an open surface of a size to receive a protruding portion of the therapeutic device while the other side is configured with an inwardly extending surface having a tapered upper end which permits ease of insertion of the device into the compartment such that as the device is inserted into the compartment the protruding portion of the device is forced into the open receiving surface and upon being fully seated the device is substantially retained within the compartment and requires canting of the device to gain release from the compartment.

13. The holder for a therapeutic device of claim 6, wherein said compartment includes a retaining member.

14. The holder for a therapeutic device of claim 13, wherein said retaining member includes a pair of opposing sides which are equipped with surfaces configured to removably secure the device within the compartment.

15. The holder for a therapeutic device of claim 14, which is further characterized such that one of said opposing sides is configured with an open surface of a size to receive a protruding portion of the housing of the therapeutic device while another of said opposing sides is configured with an inwardly extending surface having a tapered upper end which permits ease of insertion of the device into said compartment such that as the device is inserted into said compartment the protruding portion of the device is moved into the open receiving surface and upon being fully seated the device is substantially retained within said compartment and requires canting of the device to gain release from said compartment.

\* \* \* \* \*